(12) United States Patent
Williams

(10) Patent No.: US 6,528,021 B1
(45) Date of Patent: Mar. 4, 2003

(54) METHOD AND APPARATUS FOR ELIMINATING ODORS AND KILLING BACTERIA ASSOCIATED WITH EMISSIONS FROM SEWER AND GREASE TRAP VENTS

(76) Inventor: James Philip Williams, 1293 Grayson Pwy., Grayson, GA (US) 30017

( * ) Notice: Subject to any disclaimer, the term of this patent is extended or adjusted under 35 U.S.C. 154(b) by 0 days.

(21) Appl. No.: 09/928,596

(22) Filed: Aug. 13, 2001

(51) Int. Cl.[7] .............................................. B01D 53/74
(52) U.S. Cl. .................. 422/121; 422/122; 55/DIG. 30
(58) Field of Search ...................... 55/DIG. 30; 96/223, 96/224; 422/121, 123

(56) References Cited

U.S. PATENT DOCUMENTS

| | | | | |
|---|---|---|---|---|
| 3,745,750 A | * | 7/1973 | Arff | |
| 3,844,741 A | * | 10/1974 | Dimitrik | |
| 4,272,686 A | * | 6/1981 | Suzuki | |
| 5,152,814 A | * | 10/1992 | Nelson | |
| 5,316,569 A | * | 5/1994 | Heunermund | |
| 5,369,811 A | * | 12/1994 | Serre | |
| 5,656,242 A | * | 8/1997 | Morrow et al. | |
| 5,891,399 A | * | 4/1999 | Owensen | |
| 6,221,314 B1 | * | 4/2001 | Bigelow | |
| 6,287,465 B1 | * | 9/2001 | Watanabe et al. | |

* cited by examiner

Primary Examiner—Betsey Morrison Hoey

(57) ABSTRACT

The present invention provides a system and method for the treatment of hazardous biological materials being exhausted from sewer and grease trap vents. These vents may be located on the roof of public schools, commercial kitchens or multiple occupant restroom facilities. The method eliminates odors and kills bacteria associated with said emissions from sewer and grease trap vents. These emissions are neutralized when exposed to a mixture of ozone and ultraviolet radiation.

12 Claims, 5 Drawing Sheets

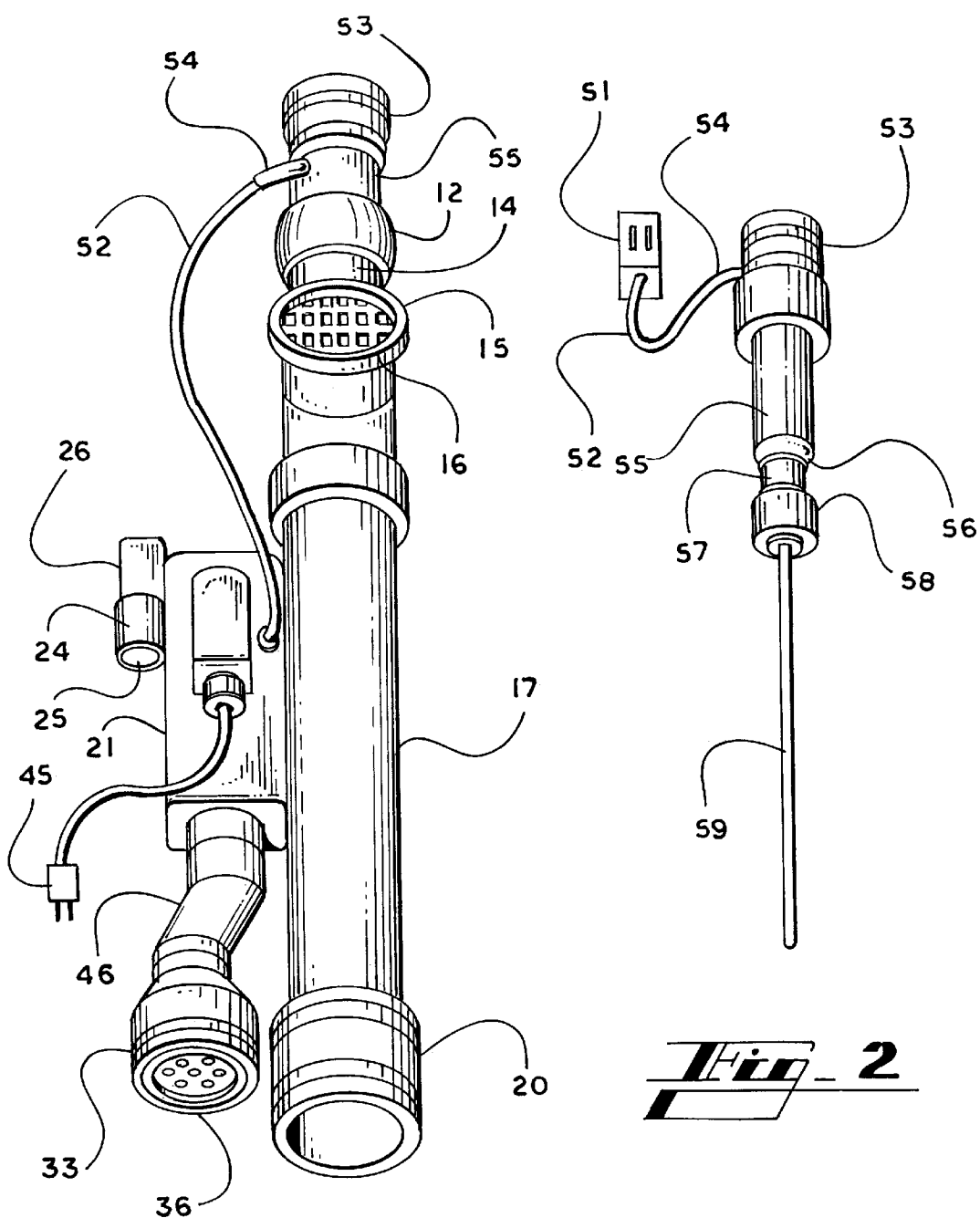

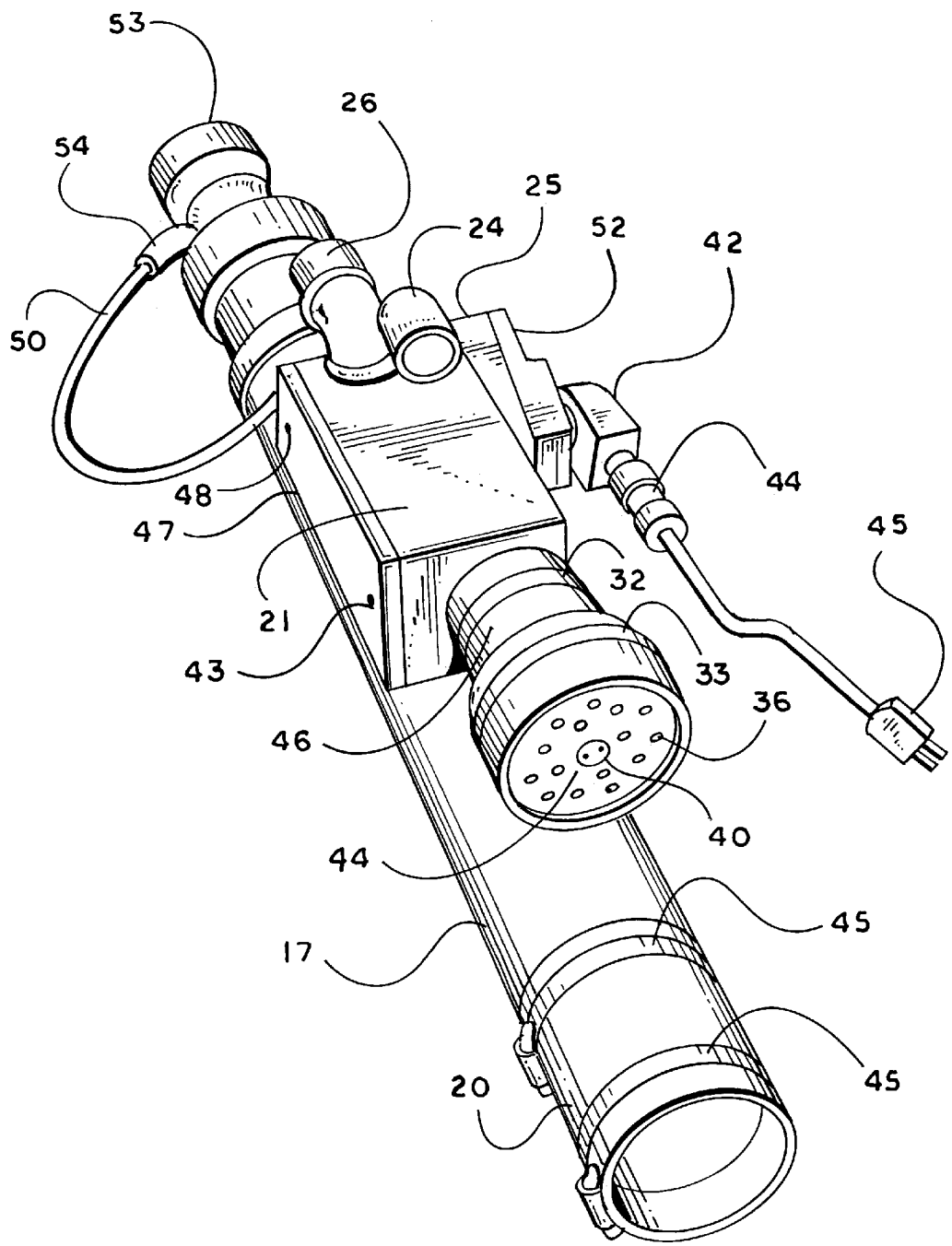
Fig_3

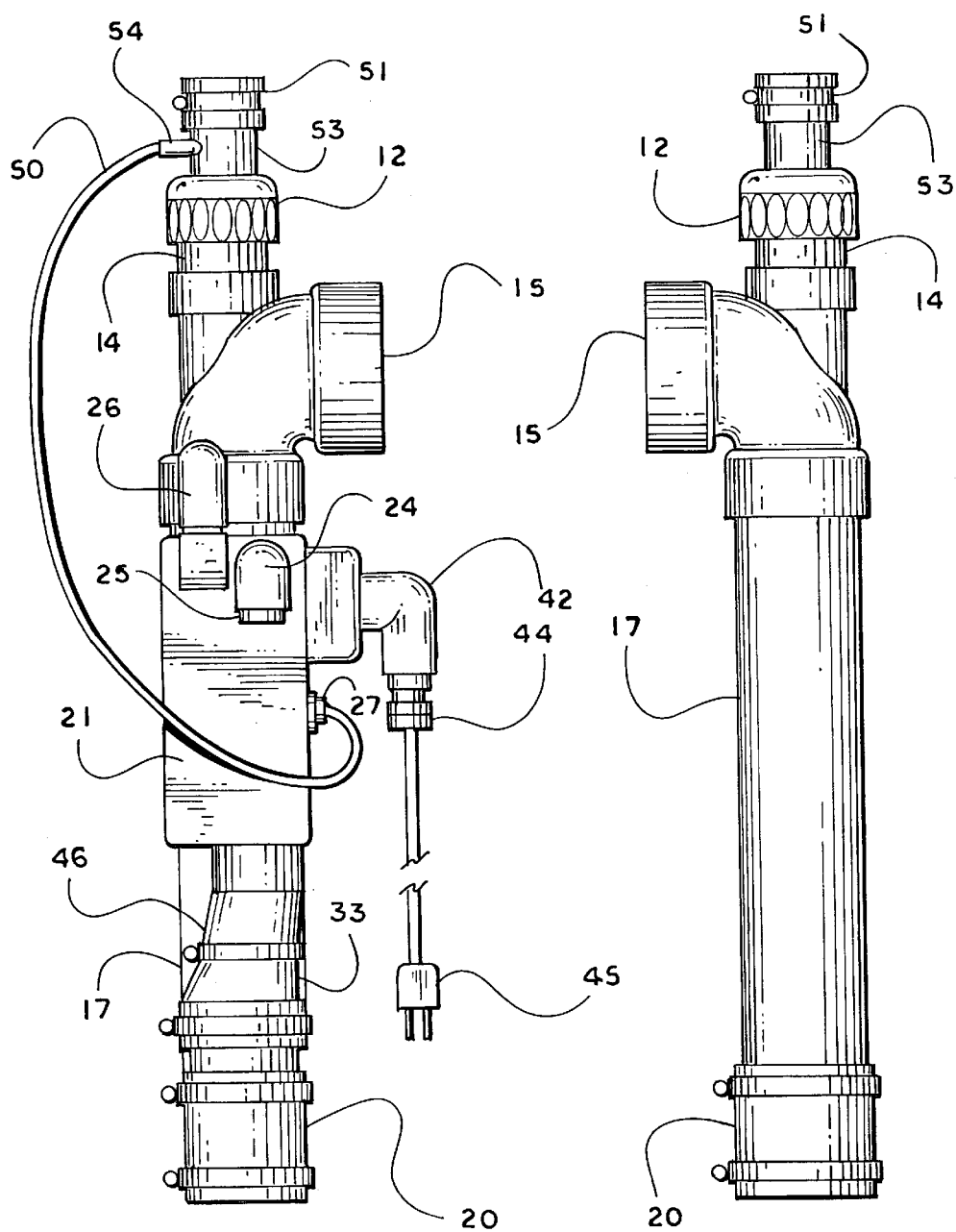

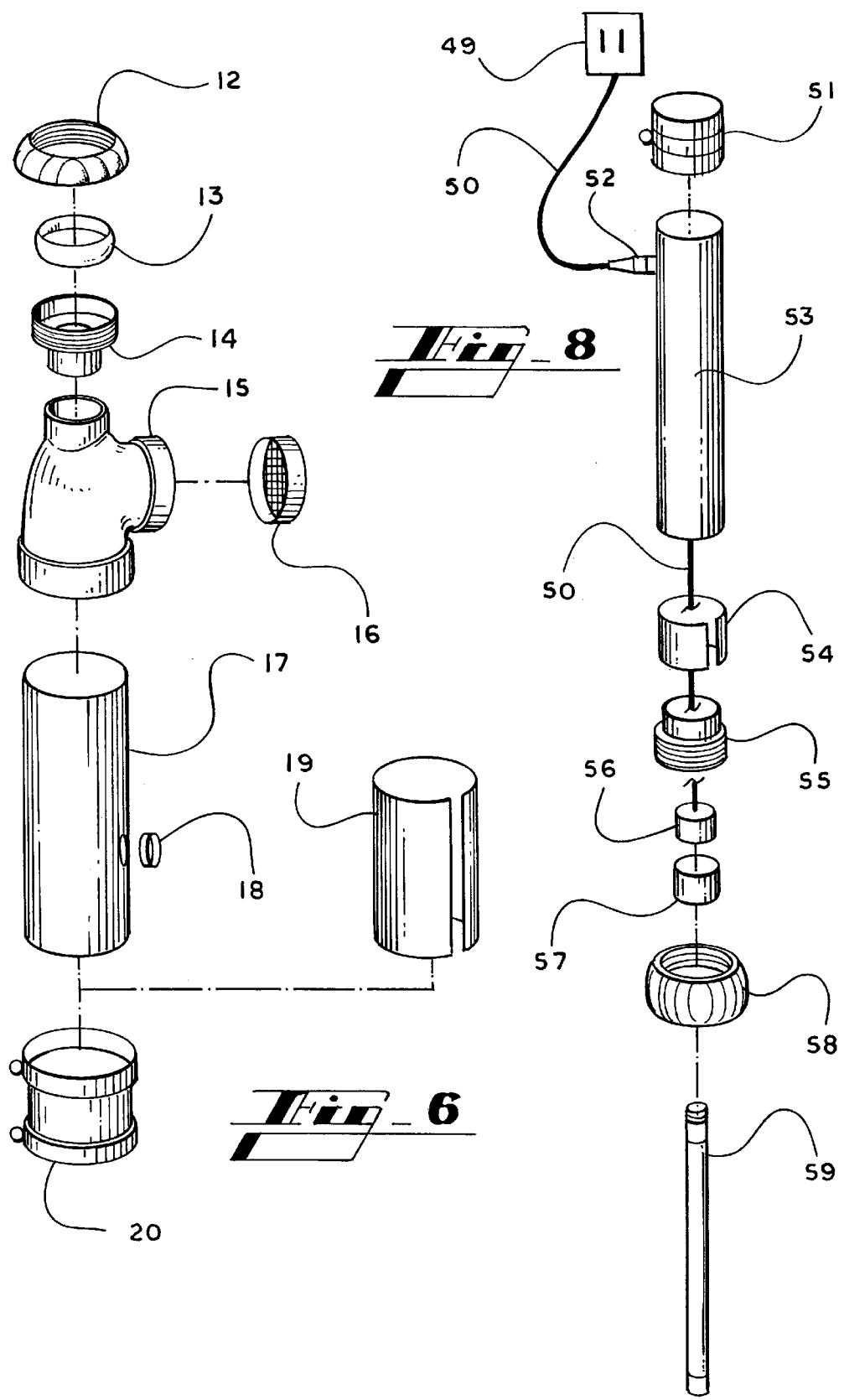

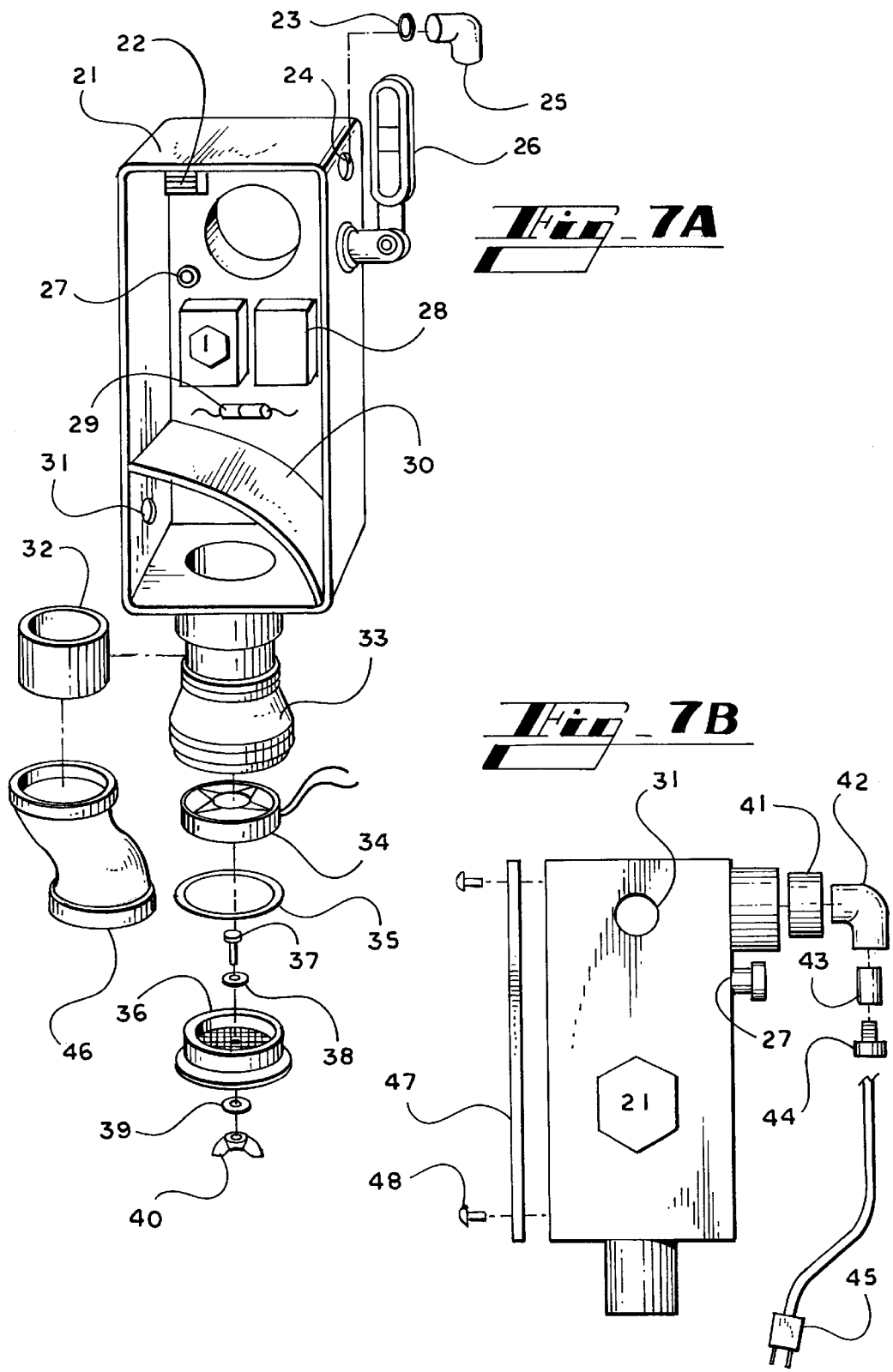

METHOD AND APPARATUS FOR ELIMINATING ODORS AND KILLING BACTERIA ASSOCIATED WITH EMISSIONS FROM SEWER AND GREASE TRAP VENTS

BACKGROUND—FIELD OF INVENTION

This invention relates to a system and method for using ultraviolet radiation and ozone. The invention may be used in the cleaning of water, sewage, and air., and more specifically with air. Air can become polluted by emissions from sewer and grease trap vents.

These emissions can be hazardous to human health. Making the air cleaner is a matter of removal of pollutants from their emissions source. There are filters and purifiers available to clean air. However, none of these address sewer and grease trap stack emissions. The present invention kills bacteria and eliminates odor from sewer and grease trap vent stacks, therefore reducing the hazards that are associated with these emissions. The treatment method is to use ozone in combination with exposure to ultraviolet radiation.

Ozone has been used for more than sixty years in Europe for the treatment of water. The role of ozone in waste fluid treatment may be classified as both an oxidant and a germicidal compound. At least four distinct recognized applications of ozone are: (1) as a bactericide; (2) as a viricide; (3) as a powerful chemical oxidant; and (4) as a promoter of hydroxyl radicals when combined with ultraviolet radiation.

The potent germicidal properties of ozone have been attributed to its high oxidation potential. Research indicates that disinfections by ozone are a direct result of bacterial cell wall disintegration. Ozone has several attributes in the treatment of waste fluids, such as odor control, color removal, and iron and manganese removal. Ozone oxidizes inorganic substances completely and rapidly, e.g., sulfides to sulfates, and nitrates to nitrites. Even greater importance lies in ozone's capability of breaking down complex organic chemicals.

BACKGROUND—DESCRIPTION OF PRIOR ART

U.S. Pat. No. 6,096,219 discloses a method and apparatus for pretreatment of hazardous waste material. This invention provided a method for pretreatment of hazardous biological and chemical contaminants from a waste fluid stream prior to discharge to a wastewater treatment facility such as a publicly owned water treatment works. The apparatus treats waste fluid streams with ozone, then exposes the mixture to ultraviolet radiation.

U.S. Pat. No. 6,156,192 is directed to a treatment system. This invention provides a waste treatment process and apparatus in which a high degree of separation is initially provided for separating solid and liquid components. Once the separator separates the solids and liquids, a fire tube combusts the solids with microwaves. The liquids are treated in a liquid treatment system which includes particle filtration/separation, and treatment with ozone and ultraviolet radiation.

U.S. Pat. No. 6,117,324 provides a system and process for treating-animal waste. Treating the wash water runoff from pen cleaning etc. It includes filtration and ozone treatment of the contaminated water through a series of three graduated holding ponds.

These three different inventions have a common goal of sewage clean up, by applying ozone combined with ultraviolet radiation.

U.S. Pat. No. 6,129,849 is directed to a process for accelerating reaction of ozone with a catalyst for the treatment of water by injection of ozone. This invention claims the removal of harmful matters, odor and color. The invention may be used for wastewater recycling of fish and farm ponds.

U.S. Pat. No. 5,935,431 is directed to a process and apparatus using ultraviolet and ozone for water purifying and for water disinfections of dental unit water supply systems.

U.S. Pat. No. 420,720 provides an ornamental design of an apparatus for the purification of water, using ultraviolet radiation and ozone. The invention may be used to clean drinking water.

All three of this group are different inventions with one common goal to clean water by applying ozone combined with ultraviolet radiation.

U.S. Pat. No. 5,972,196 is directed to the electrochemical production of ozone and hydrogen peroxide. The invention was developed to sterilize medical instruments and medical waste. It oxidizes organics found in clean up wastewater, such as laundry and food production.

U.S. Pat. No. 4,752,401 provides a water treatment system for swimming pools and potable water. The invention may be used for the treatment of re-circulated water, either potable water or for bathing, using at least one ozone producing ultraviolet lamp.

U.S. Pat. No. 5,256,379 provides an apparatus and method for removing hydrocarbons from airstreams. The apparatus and method removes hydrocarbon contaminates by flowing them into a chamber in the presence of a nozzle spraying an atomized reagent such as hydrogen peroxide and/or ozone through the air stream. The invention may be used for the clean up of contaminated soil or ground water and to flush out gasoline contaminations.

All three of this group are yet different inventions with a common use for ozone combined with ultraviolet radiation, to sterilize and remove impurities.

In conclusion, not one of these prior arts addressed sewer or grease trap emissions at the vent stack. And insofar as the inventors are aware, no sewer and grease trap vent stack emissions cleaner has formerly been developed with the combination and application presented in the present invention.

SUMMARY

This invention is a device that eliminates sewer and grease trap vented odors, and kills bacteria in the process. The device houses a combination unit that produces ultraviolet radiation and ozone. The ultraviolet lamp is contained in an elongated tube. This tube is connected to the building sewer or grease trap vent pipe and discharges treated vapors to the outside air. Attached to the outside of the elongated tube is an electrical and fan enclosure. This enclosure houses a blower fan and electrical controls. The fan draws outside air and forces it into the elongated tube, where it is exposed to ultraviolet radiation. Since sewer system exhaust is oxygen depleted, the additional outside air is important to the operation. Without the oxygen in the air that the fan forces into the unit, the ultraviolet radiation will not make the ozone needed to break down the odor causing sulfides and methane gas.

The radiation from the ultraviolet light emission kills bacteria and breaks down undesirable carbon molecules. This process eliminates most of the odors and bacteria from the sewer or grease trap vent exhaust, which prevents the discharge of dangerous vapors from accidentally being drawn into occupied spaces.

On low barometric pressure days, the undesirable vapors hug the roof line of structures and follow the movement of air, thus allowing the undesirable vapors to reenter the building or descend to the surrounding areas. This is especially true if the fresh air intakes of the ventilation system, are too close, or down wind of the sewer or grease trap vent.

The invention eliminates these odors, bacteria, and undesirable vapors. This results in a more pleasant and healthier environment. It is well known that ultraviolet light will kill bacteria, and ozone will eliminate odors. It is believed that the combination presented in this application herein has not been attempted in the past.

In the past an accepted method of stopping the outflow of offensive odors from sewer and grease trap vent pipes has been to block the outflow by the use of a one-way vent cap. This type of cap allowed the sewer system to draw in the air needed for the system to drain properly. However, this type of one-way vent cap blocks the outflow when the system needs to exhaust. Therefore, the present invention provides one or more of the following objectives: Firstly, the present invention desires not to restrict the outflow of sewer and grease trap vent pipes. It is a natural process for the sewer and grease trap to breath out as well as in. Accordingly, restricting the outflow at one point of exit will only force the pressurized gas to seek another route. It is well known that pressurized gas will force its way through plumbing systems' protective water traps and into the breathing space. Therefore the present invention desires not to restrict, but to treat the exhaust gases that contains pungent hydrocarbon, sulfides, bacteria and viruses, that can cause illness and offers a better solution than current prior art technologies.

Secondly, the present invention has been developed, tested and proven its ability to kill contaminates such as, bacteria and viruses in the exhaust of sewer and grease trap vents. The Environmental Protection Agency requires a certain amount of outside air to be brought into a building's interior. The amount of fresh air is based on the number of occupants and the type activity in the building. This air is usually filtered to catch the larger contaminants but most filters cannot stop gas, bacteria, viruses or even mold spores and pollens. This invention will reduce the amount of problem causing contaminants.

Lastly, the present invention provides an effective method for eliminating the odors being exhausted from sewer and grease trap vent pipes and not allowing them to enter the building.

BRIEF DESCRIPTION OF THE DRAWINGS

In the drawings, related FIGS. have the same numbers.

FIG. 1 shows various aspects of a frontal view of the total assembly apparatus for eliminating odors and killing bacteria associated with the emissions from sewer and grease trap vents.

FIG. 2 shows frontal view of the lamp holding section with ballast power pack and the ultraviolet lamp.

FIG. 3 shows a view of the apparatus from the bottom to the top including the electrical enclosure.

FIG. 3 also shows a view of the adjustable outside air intake.

FIG. 4 shows a right side profile with view of the electrical enclosure and fan housing section.

FIG. 5 shows a left side profile.

FIG. 6 shows a drawing of the vent pipe section.

FIG. 7A shows a drawing of the electrical and fan section facing the front opening of part 21.

FIG. 7B shows a drawing of the electrical and fan section facing the right side of part 21.

FIG. 8 shows a drawing of the lamp bulb holder section.

Parts list 1 of 3,

The Ultraviolet Bulb Housing/Vent Section.

As used herein and in the drawings, the following presents a list and brief description of the parts used in different embodiments of the present invention.

12, 13, 14 are all part of the same unit. It is one half of a rubber grommet sleeve coupling. This sleeve coupling includes three parts: 1. a receiver for a rubber bushing; 2. a rubber bushing; and 3. a pressure nut. The rubber sleeve connector comes with matching ends to repair broken pipes. The connector is cut in half and makes two 12, 13, 14 part ass emblies.

15 is a clean out Y no. C4861-CH.

16 is a snap in drain cover.

17 is a pipe, such as PVC pipe.

18 is a slant cut pipe, such as PVC pipe.

19 is a liner. The liner may be stainless steel.

20 is a flexible drain coupling. The coupling 20 may be rubber.

Parts list 2 of 3 The Electrical/Fan Sections

21 is a L.B. (left hand turn, opens on the back).

22 is a safety cut off switch.

23 is a lock nut.

24 is elbow glue.

25 is a hose st rainer washer .

26 is an optional photo control conduit mounting.

27 is a cord grip.

28 is an optional A/C to DiC adapter.

29 is a fuse holder.

30 is a plate of PVC.

34 is a hole.

32 is a section of PVC pipe.

33 is a rubber flexible drain coupling.

34 is a tube axial fan with wire leads.

35 is a bushing.

36 is an adjustable screen built from two pipe caps.

37 is a bolt.

38 are lock washers.

39 is a washer.

40 is a wing nut .

41 is a reducer plug .

42 is a street elbow.

43 is glue to thread adapter.

44 is acord grip.

45 is an extension cord.

46 is an offset PVC adapter.

47 is a cover.

48 is a cover screw.

Parts list 3 of 3, The U. V. Bulb Holder Section.

49 is an ultraviolet ballast.

50 is an electrical cord.

51 is a rubber cap.

52 is a stress relief.

53 is a pipe.

54 is a retaining ring.

55, 57, 58 are all part of the same unit. They are one half of a rubber grommet sleeve coupling. This sleeve coupling includes three parts: 1. receiver for a rubber bushing, 2. a rubber bushing, and 3. a pressure nut. The rubber sleeve connector comes with matching ends to repair broken pipes. The connector is cut in half and makes two 55, 57, 58 part assemblies.

56 is an ultraviolet bulb electrical receiver.

59 is an ultraviolet lamp bulb.

DETAILED DESCRIPTION OF THE INVENTION

The process and the apparatus description of similar parts have been indicated in the specification and drawings with the same reference numerals where appropriate. The drawings are not to scale and some sections have been enlarged for clarification purposes. All of the various controlling electrical lines have been left out for clarity.

The present invention is illustrated by the following embodiments, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

This apparatus and process being described has the capability of treating exhaust vapors from sewer and grease trap vent stacks. FIG. 1 shows a drawing describing the major components of the overall vent stack extension and ultraviolet bulb housing assembly. Specific details are shown in subsequent figures.

FIG. 2 provides a drawing describing the ultraviolet bulb holding section made of PVC pipe 55, 56 and 57. Also shown is an ultraviolet lamp bulb 59 and the ballast 51 a power supply for the bulb. Other specific details are shown in subsequent figures. FIG. 3 shows a view of the apparatus from the bottom to the top including the electrical enclosure 21 and also shows a view of the adjustable outside air intake 36.

A rubber end coupling 20 connects the device directly to the sewer or grease trap vent pipe. The bulb housing section 17 is desirably located in the main vent extension pipe. Other aspects of this unit will be discussed in subsequent figures. FIG. 4 shows a right side profile with view of the electrical enclosure 21. The fan housing unit 33 includes a rubber reducer. The top of the vent pipe assembly 15 is desirably a PVC clean out that is used to hold the lamp section and provides an exhaust port for the gases. The exhaust port is covered by a snap in drain cover 16 that is used as a pest screen. The top section 51, 53, 12, 54 and 50 are all part of FIG.2. The lamp bulb holding section will be described in detail in the parts page breakdown section.

As shown in FIG. 5, a rubber coupling 20 connects 17 the bulb housing and vent extension tube to the top of the vent stack pipe (not shown). The top of 17 is connected to the PVC Y 15 that serves as the vent stack exhaust. The top section of FIG. 2 is the lamp holding section. Details will be described in FIG. 6, FIG. 7, and FIG. 8. FIG. 6 provides a drawing of the vent pipe section containing parts 12, a pressure nut, 13, a rubber bushing and 14, a bushing receiver. 12, 13, and 14, make a receiving and locking unit for the lamp holder section shown in FIG. 8. The receiving unit 12, 13 and 14 tightens onto 53 a length of pipe. The receiving unit 12, 13 and 14, combination unit is glued into the side of 15.

Used as a bird or bug screen, 16 is a snap in drain cover. 16 glues into 15 on the side that is open to the outside air. Screen 16 protects the ultraviolet bulb. The lower remaining opening of 15 is connected to the vent pipe section 17. Out the side and up from the bottom end of 17 is 18B, a hole for receiving 18A a slant cut pipe. Outside air is forced through 18A into the U.V. light housing chamber 17. The two purposes of 18A are: 1. as a mounting ledge for 21 and 2. as an air conduit for fan 34 to deliver outside air to the ultraviolet housing chamber. A stainless steel sleeve 19 fits inside of 17 and provides a reflective, chemical resistant, cleanable surface. The vent pipe exhaust cleanup is enhanced by 19 in two ways: 1. by giving a hard cleanable surface that increases the durability of the device and 2. by reflecting the ultraviolet rays the killing capacity of the device is intensified.

At base of 17 is a flexible rubber drain coupling 20. It is used to connect 17 the vent pipe extension unit to the existing roof vent pipe stubs out (roof vent pipe stub-out not shown in diagrams).

FIG. 7A and FIG. 7B both are different perspective views of the electrical and fan section 21 and will be discussed together starting with 21 a L.B. electrical wiring pull box. Serving as the housing for the electrical components, 21 has several key devices on its outside as well as inside. Located inside is 22, a safety cut off switch, desirably with a hinge lever positioned so that when the cover plate 47 is removed the power is automatically turned off to the unit, thus protecting the service technician. The power leaves the closed safety cut off and goes through 29, a fuse and holder. 27 is a cord grip for holding and making a watertight connection on 50, which is an electrical cord 2 feet long. An optional part is 28 an ac to dc converter for use of a fan. Another optional part, 26, is a photo control, for when night time use is not desired.

Providing the u.v. light chamber with outside air is a tube axial fan with wire leads 34. It may be a ball bearing fan. It provides an airflow to the device as needed. The air is forced through 18A and into air chamber 17. The electrical housing box 21 has a cooling system. The cooling system may include a deliberate air leak around the air chamber block 30 past the electrical components and out the side close to the top; a combination unit of a lock nut 23 and a street elbow 24 and a hose strainer washer 25 used to keep out pests. Without this coolant system some of the electrical components might overheat and fail. Failures cause unnecessary down time, undue expense and dissatisfied customers.

The outside air provided by the fan 34 is moved through the air chamber in 21 and is directed toward the air duct 31 by the air block 30 a curved section of PVC (poly vinyl chloride) pipe.

The outside air is pushed through 31, 18A and 18B into the ultraviolet light and vent exhaust chamber. In this chamber the ultraviolet lamp is bathed with the oxygen needed to generate ozone, which helps eliminate odors. 32 is a section of PVC pipe that connects 21 to 46, an off set PVC adapter. The offset in 46 connects and provides the necessary room for 33 the fan housing to stand out and away from 17 the lamp and vent housing.

The fan 35 is held in place by 34, a retainer ring cut from PVC pipe. The fan 35 is protected from pests by a dual purpose adjustable screen 36. This adjustable screen keeps out pests such as bees, birds, etc. and allows the amount of outside air being drawn in to be adjusted. The adjustable screen 36 may be constructed of two PVC test caps connected by a bolt 37, lock washer 38, fender washer 39 and wing nut 40 in combination. This screen unit has holes 20 to allow the outside air to pass through, yet screening out pests.

The electrical cord 45, an extension cord with ground, is held in place by 44, a cord grip. 44 is connected to 43 a thread adapter bushing. 43 is connected to 42, a PVC street elbow. Component 41, a PVC reducer, connects 42 to 21, the LB electrical enclosure. The last of these components is 47, the L.B. enclosure lid held in place by cover screws 48.

FIG. 8 shows the lamp bulb holding section. This breakdown depicts an ultraviolet ballast 49, which is the power supply for the ultraviolet light bulb. An electrical cord 50 comes with the ballast. This cord is passed through 52, a stress relief and ends at 56, an ultraviolet bulb electrical receiver 59. The receiver holds an ultraviolet lamp bulb that plugs into 56. At the top of the unit is 51, a rubber cap. This cap closes off pipe 53 to protect the bulb's electrical connection from moisture.

Next is a reducing/retaining ring 54, structured from PVC pipe with a partial section removed. The receiver 55 of the 55, 57, 58 bulb-holding combo, is recessed and glued inside the reducing ring 54, then glued into 53.

The 55, 57, 58 bulb holding combo is actually, one half of a rubber grommet sleeve coupling. This union includes three parts: 1. a receiver for a rubber bushing, 2. a rubber bushing, and 3. a pressure nut. The rubber sleeve connector comes with matching ends to repair broken pipes. The rubber sleeve connector is cut in half and makes two 55, 57, 58 part assemblies.

What is claimed is:

1. A method for treating gases, wherein the gases are sewer gas emissions or grease trap emissions comprising:

providing a housing having an ultraviolet radiation source;

flowing a gas to be treated into the housing;

providing a source of oxygen into the housing;

irradiating the oxygen with the ultraviolet radiation source to form ozone; and treating the gas by application of the ozone and ultraviolet radiation;

wherein the gas to be treated includes odors, bacteria, viruses, pollutants, or a combination thereof;

further wherein the odors, bacteria, viruses, pollutants, or a combination thereof are substantially eliminated after treatment with the ozone, ultraviolet radiation or a combination thereof to provide a treated gas.

2. The method of claim 1, wherein the gases are sewer gas emissions.

3. The method of claim 1, wherein the gases are grease trap emissions.

4. The method of claim 1, wherein the odors are selected from methane gas; sulfides, nitrates, or a combination thereof.

5. The method of claim 1, wherein the pollutants are selected from hydrocarbons, complex organic chemicals, or a combination thereof.

6. The method of claim 1, wherein the source of oxygen comprises air.

7. The method of claim 1, wherein the housing further includes a fan for drawing the air into the housing.

8. The method of claim 7, wherein the housing further includes an adjustable screen.

9. The method of claim 1, wherein the housing further includes an electrical housing box for holding electrical components.

10. The method of claim 9, wherein the electrical housing box further includes an AC to DC converter.

11. The method of claim 9, wherein the electrical housing box further includes a photo control.

12. The method of claim 9, wherein the electrical housing box further includes a cooling system.

* * * * *